US012574980B2

(12) United States Patent (10) Patent No.: US 12,574,980 B2
Raso et al. (45) Date of Patent: Mar. 10, 2026

(54) SYSTEM AND METHOD FOR PAIRING DEVICES IN A GYM ENVIRONMENT

(71) Applicant: Polar Electro Oy, Kempele (FI)

(72) Inventors: Andrea Raso, Fleurier (CH); Jukka Happonen, Kempele (FI); Michael Lutz, Fleurier (CH); Sami Karvonen, Fleurier (CH)

(73) Assignee: Polar Electro Oy, Kempele (FI)

( * ) Notice: Subject to any disclaimer, the term of this patent is extended or adjusted under 35 U.S.C. 154(b) by 415 days.

(21) Appl. No.: 18/114,182

(22) Filed: Feb. 24, 2023

(65) Prior Publication Data

US 2023/0300918 A1 Sep. 21, 2023

(30) Foreign Application Priority Data

Mar. 1, 2022 (EP) .................................... 22159417

(51) Int. Cl.
*H04W 76/14* (2018.01)
*A61B 5/00* (2006.01)
*G01S 5/14* (2006.01)
*H04W 4/021* (2018.01)

(52) U.S. Cl.
CPC .......... *H04W 76/14* (2018.02); *A61B 5/0002* (2013.01); *A61B 5/681* (2013.01); *G01S 5/14* (2013.01); *H04W 4/021* (2013.01); *A61B 2503/10* (2013.01); *G01S 2205/08* (2020.05)

(58) Field of Classification Search
CPC ... A61B 2503/10; A61B 5/0002; A61B 5/681; G01S 2205/08; G01S 5/14; H04W 4/021; H04W 4/33; H04W 4/38; H04W 4/80; H04W 76/14
See application file for complete search history.

(56) References Cited

U.S. PATENT DOCUMENTS

2013/0178334 A1* 7/2013 Brammer ........... A63B 71/0622
482/4
2015/0382150 A1 12/2015 Ansermet et al.
2016/0346617 A1 12/2016 Srugo et al.
2021/0205663 A1* 7/2021 Blahnik ................. G16H 50/30
2022/0022007 A1 1/2022 Tsai et al.

OTHER PUBLICATIONS

Extended European Search Report for EP Patent Application Serial No. 22159417.9 dated Jul. 12, 2022, 4 pages.

\* cited by examiner

*Primary Examiner* — Timothy X Pham
(74) *Attorney, Agent, or Firm* — FisherBroyles, LLP

(57) ABSTRACT

A system and method pairs devices in a gym environment. The system includes: a server computer; a plurality of data collector devices, each of the plurality of data collector devices being associated with a gym device or an exercise spot of a gym, wherein each data collector device includes a wireless communication unit, and a memory configured to store training data of a user; one or more time-of-flight positioning units configured to be disposed at fixed locations in the gym and conduct time-of-flight positioning; one or more mobile tag devices, each mobile tag device comprising a time-of-flight positioning unit configured to conduct the time-of-flight positioning together with the time-of-flight positioning units at the fixed locations; and one or more wearable devices, wherein each wearable device is associated with one of the one or more mobile tag devices.

16 Claims, 5 Drawing Sheets

START

200 CONDUCT TIME-OF-FLIGHT POSITIONING

202 TRACK LOCATIONS OF MOBILE TAG DEVICES

204 DETERMINE IF TAG IN PAIRING AREA

TAG IN PAIRING AREA?

YES    NO

206 TRIGGER WIRELESS CONNECTION

208 TRANSMIT TRAINING DATA

END

SYSTEM AND METHOD FOR PAIRING DEVICES IN A GYM ENVIRONMENT

CROSS-REFERENCE TO RELATED APPLICATION

This application claims benefit and priority to European Application No. 22159417.9, filed Mar. 1, 2022, which is incorporated by reference herein in its en-tirety.

BACKGROUND

Field

Various embodiments relate to a system and a method for pairing devices in a gym environment.

SUMMARY

An athlete may log exercise-related data and exchange it between multiple devices in a gym environment. The data may originate from various sources, such as from the athlete's personal measurement devices, from gym equipment like a treadmill or a spinning bike, or from a central server. As an example, the athlete may wish to exchange data between their personal heart rate monitor and a treadmill for the purpose of displaying their heart rate on a display of the treadmill. To enable exchange of data between two sources or devices, the devices must be paired to one another in some way. Current techniques related to automatic pairing of devices include selecting a nearby device to pair with using signal strength-based metrics, such as received signal strength indication (RSSI). However, such metrics may be sensitive to disturbances, and their accuracy may be insufficient in a crowded gym environment. Due to this, automatic pairing may not occur when expected, or unintended pairing may occur unexpectedly.

According to an aspect, there is provided subject matter of independent claims. Dependent claims define some embodiments.

One or more examples of implementations are set forth in more detail in the accompanying drawings and the description of embodiments.

BRIEF DESCRIPTION OF THE DRAWINGS

Some embodiments will now be described with reference to the accompanying drawings, in which.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Reference numbers, both in the description of the embodiments and in the claims, serve to illustrate the embodiments with reference to the drawings, without limiting it to these examples only.

The embodiments and features, if any, disclosed in the following description that do not fall under the scope of the independent claims are to be interpreted as examples useful for understanding various embodiments of the invention.

Figures 1, 2:
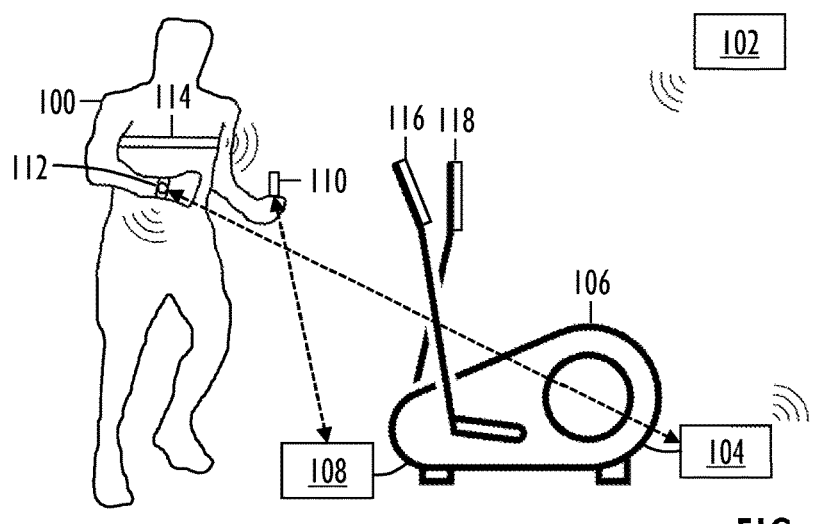
FIG. 1 illustrates embodiments of a system.
FIG. 2 illustrates embodiments of a method.

Let us describe an exemplary scenario in a gym environment with reference to FIG. 1. A gym typically has multiple gym devices or exercise spots, including treadmills, stationary bicycles, elliptical trainers, rowing machines, weight machines, and/or free-weight training spots, for example. A user 100 is planning to work out and approaches a gym device 106, illustrated as an elliptical trainer. The user is wearing a wearable devices 112, 114, specifically a portable training computer on his wrist, and a heart rate monitor 114 attached to his chest with a chest strap. The user is also carrying a mobile tag device 110 in his hand. The elliptical trainer 106 comprises electrocardiogram (ECG) sensors 116, 118 configured to measure an ECG of the user while the user is exercising on the elliptical trainer. The elliptical trainer is coupled to a data collector device 104 and a time-of-flight positioning unit 108. A server 102 is also provided in the gym environment.

According to an aspect, a system for pairing devices in a gym environment comprises a server computer 102 comprising at least one processor and at least one memory configured to store training data of one or more users; a plurality of data collector devices 104, each of the plurality of data collector devices being associated with a gym device 106 or an exercise spot of a gym, wherein each data collector device comprises a wireless communication unit, and a memory configured to store training data of a user 100; one or more time-of-flight positioning units 108 configured to be disposed at fixed locations in the gym and conduct time-of-flight positioning; one or more mobile tag devices 110, each mobile tag device comprising a time-of-flight positioning unit configured to conduct the time-of-flight positioning together with the time-of-flight positioning units at the fixed locations; and one or more wearable devices 112, wherein each wearable device is associated with one of the one or more mobile tag devices, and each wearable device comprises a wireless communication unit, and a memory configured to store training data of the user. The system is configured to: track locations of the one or more mobile tag devices with respect to the data collector devices in the gym as a result of the time-of-flight positioning; determine, on the basis of the tracking, whether or not a location of a mobile tag device is within a pairing area of a data collector device; and if the location is determined to be within the pairing area, trigger establishment of a wireless connection between a wireless communication unit of the data collector device and a wireless communication unit of a wearable device associated with the mobile tag device, and transmit training data between at least two of the data collector device, the wearable device, and the server computer.

FIG. 2 illustrates embodiments of a method for pairing devices in a gym environment. According to an aspect, the method comprises: conducting 200 time-of-flight positioning, by one or more mobile tag devices together with one or more time-of-flight positioning units, wherein the one or more time-of-flight positioning units are configured to be disposed at fixed locations in a gym; tracking 202 locations of the one or more mobile tag devices with respect to a plurality of data collector devices in the gym as a result of the time-of-flight positioning, wherein each of the plurality of data collector devices is associated with a gym device or an exercise spot of a gym and configured to store training data of a user; determining 204, on the basis of the tracking, whether or not a location of a mobile tag device is within a pairing area of a data collector device; and if the location is determined to be within the pairing area, triggering 206 establishment of a wireless connection between a wireless communication unit of the data collector device and a wireless communication unit of a wearable device configured to store training data of the user and associated with the mobile tag device, and transmitting 208 training data between at least two of the data collector device, the wearable device, and a server computer configured to store training data of one or more users.

Advantages of the system and method described above include improved reliability when compared to RSSI-based pairing. As a wireless communication environment, gyms have been discovered to have significant multi-path characteristics. When estimating distances or locations, time-of-flight positioning is more resistant in multi-path environments when compared to approaches based on signal strength.

Another advantage is improved accuracy of the positioning. The accuracy of signal strength-based positioning may be in the order of metres (m), such as 1-5 m for Bluetooth positioning systems, 5-15 m for Wi-Fi positioning systems, and up to 1 m for radio frequency identification (RFID) positioning. As an example of time-of-flight positioning, the accuracy of ultra-wideband (UWB) positioning may be in the order of 10 centimetres (cm).

Further, some Bluetooth devices may not provide transmission (Tx) power in their Bluetooth advertisements, which may complicate using Bluetooth positioning with such devices.

Both the improved reliability and improved accuracy may reduce the likelihood of unintended pairing of the wearable device to a data collector device. Similarly, they may increase the likelihood of successful automatic pairing. As a result, the user's wearable device may pair with the data collector device of the gym device or exercise spot that the user is using for data transmission between the data collector device, the wearable device, and/or the server computer.

Yet further advantages of time-of-flight positioning are real-time positioning and reduced power consumption when compared to the alternatives discussed above.

The server computer may be a local server computer provided at the gym, such as the server computer 102 illustrated in FIG. 1. Alternatively or additionally, the server computer may be, or it may be coupled to, a remote (cloud) server provided outside of the gym.

The server computer stores training data of one or more users, including the user 100. The training data may be user-specific, and the training data of each user of the one or more users may be identified by an identifier (ID) associated with the training data of the user. The ID may be a user ID identifying the user, or a device ID identifying a device of the user, for example. The training data may include training plans, user-specific training configurations, training logs, and/or data measured from the user.

The training plans may comprise long-term training plans, each plan outlining a training program to be performed over a period of e.g. several days or months. The training plans may also comprise training session plans that each outline a training session program to be performed in one training session by the user.

The user-specific training configurations may include user-specific heart rate zones, personal records, activity targets, and personal information such as age, date of birth, weight, and/or height. The personal information may be relevant when computing the energy (calorie) consumption of the user during training, for example.

The training logs may include records of past training sessions completed by the user.

The data measured from the user may include data measured by one or more biosensors. The biosensors may comprise one or more of the following: one or more heart activity sensors, one or more motion sensors, one or more location sensors, one or more swimming sensors, one or more power sensors, one or more bike sensors, and/or one or more temperature sensors.

The heart activity sensors may be configured to determine heart activity, such as heart rate, heart beat interval (HBI) and/or heart rate variability (HRV), for example. The heart activity sensors include, but are not limited to, a cardiovascular sensor (such as an ECG sensor), an optical heart activity sensor such as a photoplethysmography (PPG) sensor, or a bioimpedance plethysmography. The optical heart activity sensor may detect the heart activity of the user by optical heart rate measurement, which may comprise sending a light beam towards skin of the user and measuring the bounced and/or emitted light from the skin of the user. The light beam may alter when travelling through veins of the user and the alterations may be detected by the optical heart rate activity sensor. The ECG sensor may be integrated to the heart rate monitor belt 114 or to a gym device 106 like the elliptical trainer of FIG. 1 as ECG sensors 116, 118, and the PPG sensor to the wearable device 112, for example. Further, besides these types of heart activity sensors, other types of biosignal measurement sensors may be embedded into the heart activity sensors. These types include but are not limited to the following: a Laser Doppler-based blood flow sensor, a magnetic blood flow sensor, an electromechanical film (EMFi) pulse sensor, a polarization blood flow sensor. In an embodiment, the heart activity sensor may produce raw sensor data of the heart activity and/or it may process the sensor data into heart activity information, such as heart rate, for example.

Motion sensors may be configured to measure motion induced by the user to the motion sensors by moving their hands, chest, head, or other body parts to which the motion sensor attached to. The motion sensor may use other motion data, such as location data of the user, to determine motion of the user. In an example embodiment, the motion sensor comprises at least one of the following: an accelerometer, a magnetometer, and a gyroscope. The motion sensor may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

Location sensors may utilize a global navigation satellite system (GNSS) or other satellite-based, or radio system-based system for locating the user and measuring various parameters (speed, distance, location, route) relating to the movement of the user.

Swimming sensors may measure swimming specific parameters such as number of strokes or distance, for example.

Bike sensors may be sensors attached to various parts of a (stationary) bike for measuring speed, cadence, or power, for example.

The sensor data measured by the sensors, or determined by the apparatus on the basis of the sensor data, may comprise: heart rate zones, heart rate samples, heart rate variation samples, heart beat interval samples, fat consumption rate, calorie consumption rate, consumed amount of calories, activity zones, activity samples, speed and/or pace samples, power samples, cadence samples, altitude samples, temperature samples, location samples, distance elapsed, time elapsed, pedal index, left-right balance, running index, training load, galvanic skin response samples, fluid balance, skin temperature samples, heading samples and/or bike angles. The location data may comprise satellite positioning data, such as, GNSS positioning data, or any other data that allows the determination of the location of the user during the exercise at any given time. Movement indoors may be detected via indoor location tracking methods, such as mapping techniques including measuring Earth's magnetic fields or radio frequency signals.

The plurality of data collector devices are each associated with a gym device or an exercise spot of the gym. In an embodiment, the data collector device is comprised in the gym device or exercise spot that the data collector device is associated with. Each data collector device comprises a wireless communication unit, and a memory configured to store training data of a user. The data collector device may be configured to store training data of one user at a time. As described above, the training data may include training plans, user-specific training configurations, training logs, and/or data measured from the user.

In an embodiment, the plurality of data collector devices are configured to acquire training data of the user. A data collector device of the plurality of data collector devices may acquire the training data from the gym device or exercise spot associated with the data collector device, from the wearable device, from the server computer, and/or using the wireless communication unit of the data collector device, for example.

The associations between the data collector devices and the gym devices or exercise spots may be stored in the memory of the server computer, the memories of the data collector devices, and/or the memories of the wearable devices, for example. The memory of a data collector device may comprise a gym device or exercise spot identifier of the gym device or exercise spot associated with the data collector device. Alternatively or additionally, the server computer may store all the associations between the data collector devices and the gym devices or exercise spots.

In an embodiment, the data collector device is configured to store training data of the user of the wearable device during the wireless connection. The data collector device may be configured to detect termination of the wireless connection, and to delete the training data of the user as a result of the termination. To account for temporary disruptions in the wireless connection, the data collector device may be configured to delay the deleting by a predetermined time, such as 1 minute, and cancel the deleting if the wireless connection is resumed during the predetermined time.

In an embodiment, the data collector device 104 is coupled to one or more biosensors 116, 118 of a gym device associated with the data collector device, the one or more biosensors configured to measure the user to acquire training data, and wherein the data collector device is configured to transmit the training data to the wearable device over the wireless connection and/or to the server computer. In FIG. 1, the biosensors 116, 118 are ECG sensors configured to measure an ECG of the user. The data collector device may receive the training data from the one or more biosensors, i.e. the ECG sensors, via a wired connection to the gym device and/or the associated one or more biosensors, as shown in FIG. 1. Alternatively or additionally, the data collector device may receive the training data from the one or more biosensors via a wireless connection using the wireless communication unit of the data collector device. The one or more biosensors may comprise one or more of the following: one or more heart activity sensors, one or more motion sensors, one or more location sensors, one or more swimming sensors, one or more power sensors, one or more bike sensors, and/or one or more temperature sensors, embodiments of which have been discussed in more detail above.

The data collector device may receive training data from its associated gym device, from the biosensors and/or other components of the gym device. When the gym device is a treadmill, the training data received form the gym device may include speed information, user's weight information, pressure information indicating user's location on the treadmill, incline/recline values, and/or proximity sensor data indicating whether the user on the equipment or not. When the gym device is an exercise bicycle, the training data received from the gym device may include resistance, speed, and/or cadence information. When the gym device is an elliptical trainer, the training data received from the gym device may include resistance, speed, and/or cadence information. When the gym device is a stepper device, the training data received from the gym device may include speed, user's weight, and/or step length. When the gym device is a rowing machine, the training data received from the gym device may include resistance values, speed (strides/minute), motion length, etc.

The one or more time-of-flight positioning units 108 are configured to be disposed at fixed locations in the gym. The fixed locations may include the locations of gym devices or exercise spots associated with the data collector devices. Further, the one or more time-of-flight positioning units may be comprised in the gym devices.

Figures 3, 4:
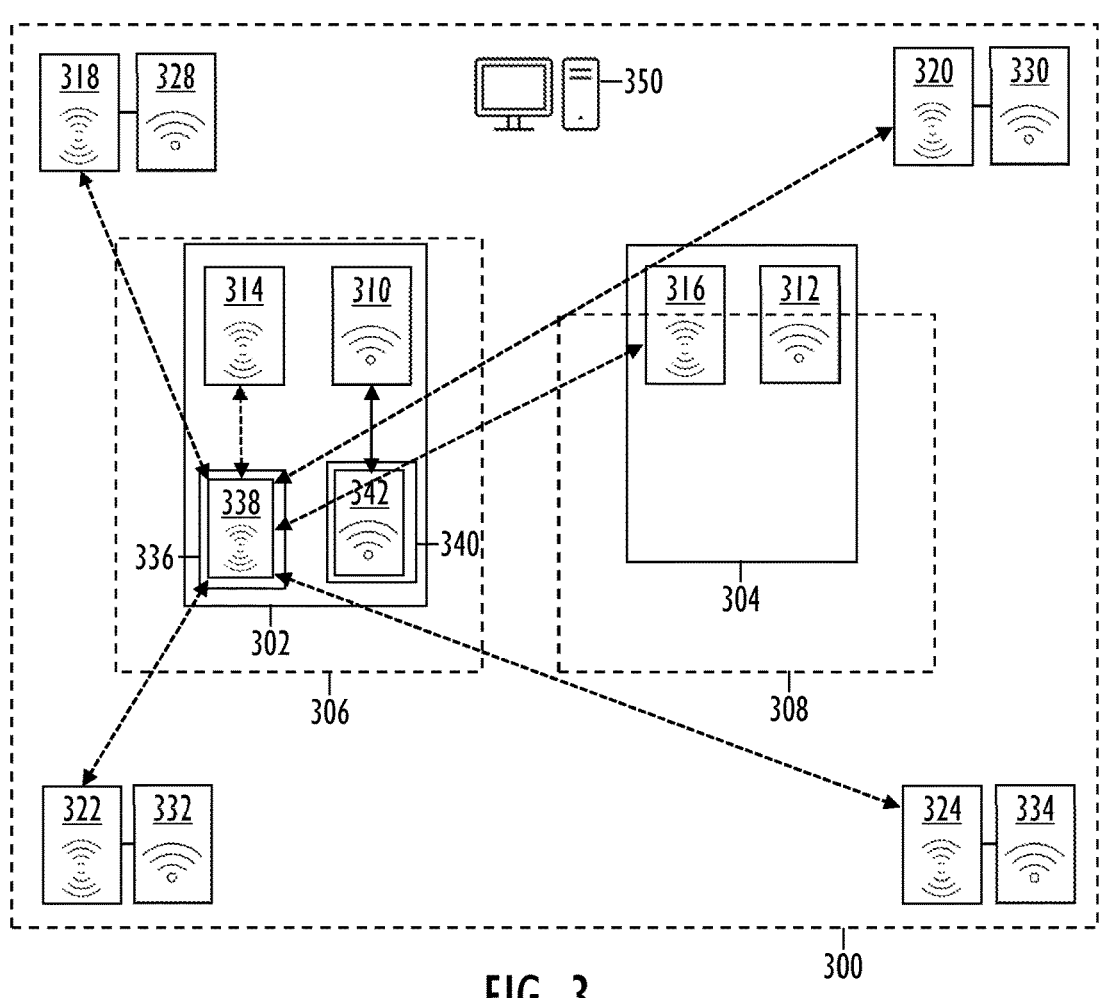
FIG. 3 illustrates embodiments of a system in a gym environment.
FIG. 4 illustrates embodiments related to placement of gym devices.

FIG. 3 illustrates embodiments of the system in a gym environment. A server computer 350 is located in the gym. The gym 300 has two gym devices 302 and 304. The gym device 304 has a pairing area 306, and the gym device has a pairing area 308. Each gym device 302, 304 is at least partially located in its respective pairing area 306, 308. Gym device 302 is located entirely in its pairing area 306, and gym device 304 is partially located in its pairing area 308. The gym devices 302, 304 comprise data collector devices (not shown) including wireless communication units 310 and 312. The gym devices further comprise time-of-flight positioning units 314 and 316. Time-of-flight positioning units 318, 320, 322, and 324 are disposed in fixed locations in the corners of the gym. The time-of-flight positioning units 318, 320, 322, and 324 may comprise or be coupled to wireless communication units 328, 330, 332, and 334. A mobile tag device 336 comprising a time-of-flight positioning unit 338 is in the pairing area 306 of the gym device 302. A wearable device 340 with a wireless communication unit 342 is associated with the mobile tag device 336. The wearable device 340 is also located in the pairing area 306 of the gym device 302. The time-of-flight positioning unit 338 of the mobile tag device 336 together with the time-of-flight positioning units 314, 316, 318, 320, 322, 324 conduct time-of-flight positioning. The system tracks locations of the mobile tag device 336 with respect to the data collector devices comprised in the gym devices 302, 304. The system determines that the location of the mobile tag device 336 is within the pairing area 306 of the data collector device, and triggers establishment of a wireless connection between the wireless communication unit 310 of the data collector device and the wireless communication unit 342 of the wearable device 340. The system then transmits training data between at least two of the data collector device, the wearable device 340, and the server computer 350.

In an embodiment, at least one of the one or more time-of-flight positioning units is configured to be disposed at a fixed location of a gym device or an exercise spot associated with the plurality of data collector devices. In an embodiment, the one or more time-of-flight positioning units comprises a plurality of time-of-flight positioning units 314, 316 that are configured to be disposed at fixed locations of each gym device 302, 304 or exercise spot associated with the plurality of data collector devices. Each gym device or exercise spot may therefore have a time-of-flight positioning unit at its location. The accuracy of the time-of-flight positioning may be improved, and the likelihood of pairing the correct data collector device and mobile tag device may be increased. In an embodiment, each gym device comprises the time-of-flight positioning unit configured to be disposed at the location of the gym device. The server computer, the time-of-flight positioning units, and/or the data collector devices associated with the gym devices or exercise spots may store associations between the time-of-flight positioning units and the data collector devices. Tracking the locations of the one or more mobile tag devices may be simplified, as the locations may be treated as distances or proximities to the plurality of time-of-flight positioning units 314, 316 that are configured to be disposed at fixed locations of each gym device or exercise spot. In an embodiment, each time-of-flight positioning unit of the plurality of time-of-flight positioning units 314, 316 that are configured to be disposed at fixed locations of each gym device 302, 304 or exercise spot associated with the plurality of data collector devices are configured to track the locations of the one or more mobile tag devices, and the time-of-flight positioning unit or a data collector device associated with the gym device 302, 304 or exercise spot whose fixed location the time-of-flight positioning unit is disposed at is configured to determine, on the basis of the tracking, whether or not a location of a mobile tag device is within a pairing area of the data collector device; and if the location is determined to be within the pairing area, the data collector device is configured to trigger establishment of the wireless connection.

In an embodiment, the one or more time-of-flight positioning units 318, 320, 322, 324 are configured to be disposed at fixed locations separate from the locations of each gym device 302, 304 or exercise spot associated with the plurality of data collector devices. The one or more time-of-flight positioning units may therefore be disposed in convenient locations in the gym. The locations of the one or more time-of-flight positioning units may also be selected to optimize positioning accuracy of the time-of-flight positioning. In an embodiment, the one or more time-of-flight positioning units comprise a plurality of time-of-flight positioning units comprising at least three time-of-flight positioning units; each of the at least three time-of-flight positioning units configured to be located at a vertex of a virtual polygon in the gym. In an embodiment, the plurality of time-of-flight positioning units comprises three time-of-flight positioning units, and the virtual polygon is a virtual rectangular cuboid, or a virtual cube. 'Virtual' described herein is to be understood so that e.g. a 'virtual cube' is an imaginary cube whose vertices may be used to determine the positions of the time-of-flight positioning units as described above.

It is noted that the plurality of time-of-flight positioning units need not be positioned along one line or plane; for example, a first set of time-of-flight positioning units may be configured to be disposed on a first floor of the gym, and a second set of time-of-flight positioning units may be configured to be disposed on a second floor of the gym.

In general, one time-of-flight positioning unit of the one or more time-of-flight positioning units may determine a distance to a mobile tag device. The one time-of-flight positioning unit may thus track the location of the mobile tag device in three-dimensional (3D) space to a radius measured from the one time-of-flight positioning unit, equivalent to the surface of a sphere with its centre at the location of the time-of-flight positioning unit. However, it remains uncertain what point along the radius or surface of the sphere the mobile tag device is located at. In two-dimensional (2D) space, one time-of-flight positioning unit may track the location of the mobile tag device to a circumference of a circle with its centre at the location of the time-of-flight positioning unit. Two time-of-flight positioning units may track the location of the mobile tag device to a circumference of a circle in 3D space, and to a pair of points in 2D space. If the location tracking is sufficiently constrained or if the mobile tag device and the two time-of-flight positioning units are all located along a straight line, the location of the mobile tag device may be tracked exactly to a single point in 2D space. Three time-of-flight positioning units may track the location of the mobile tag device to a single point in 3D space. Further time-of-flight positioning units may improve the accuracy, range and/or resolution of the positioning and location tracking.

FIG. 4 illustrates embodiments related to the placement of gym devices and exercise spots in the gym. In an embodiment, each gym device 400, 402, 404 or exercise spot associated with a data collector device is disposed in the gym such that the gym device or exercise spot is at a unique distance 410, 412, 414 from a time-of-flight positioning unit 420 with respect to the other gym devices and exercise spots, and the pairing area of the data collector device associated with the gym device or exercise spot comprises a range of distances 422, 424, 428 between the mobile tag device and the time-of-flight positioning unit including the unique distance. For example, the unique distance to a gym device may be 10 m, and the pairing area for the gym device may comprise the range of distances from 9 m to 11 m. The embodiment may be most useful in a long, narrow gym wherein the gym devices or exercise spots are most convenient to arrange substantially in a line. However, such an arrangement is not strictly necessary as long as each gym device or exercise spot is disposed in the gym such that the gym device or exercise spot is at a unique distance from the time-of-flight positioning unit with respect to the other gym devices and exercise spots. In an embodiment, the one or more time-of-flight positioning comprise only one time-offlight positioning unit, i.e. the time-of-flight positioning unit relative to which the gym devices or exercise spots are located at unique distances.

In an embodiment the pairing areas of the plurality of data collector devices are non-overlapping. Conflicting situations wherein a mobile tag device is simultaneously located in a pairing area of a first data collector device and a pairing area of a second data collector device may be avoided. Alternatively, the system may utilize rules based on e.g. a ranking of the data collector devices, and/or distances measured by the time-of-flight positioning, to determine which of the first and second data collector devices to pair with the mobile tag device.

Each mobile tag device of the one or more mobile tag devices 110 comprising a time-of-flight positioning unit configured to conduct the time-of-flight positioning together with the time-of-flight positioning units at the fixed locations. A mobile tag device may be small, portable device intended to be carried by the user. Alternatively or additionally, the mobile tag device may be integrated to another device, such as a smartphone. It is assumed that the user carries the mobile tag device with them when using the gym devices and/or exercise spots at the gym. Therefore, the location of the mobile tag device may be assumed to represent the location of the user. Further, the location of the wearable device(s) worn by the user may be deduced or assumed to be the same as the location of the mobile tag device.

The time-of-flight positioning may be implemented in several ways, some of which are known in the art. One technique is based on time difference of arrival (TDoA). The TDoA technique may be applied to the system described herein by using the time-of-flight positioning units disposed at fixed locations as anchors. The time-of-flight positioning units may be synchronized to run on the same clock. The time-of-flight positioning units may detect locations of the mobile tag devices by analysing differences in arrival times of signals transmitted by the mobile tag devices.

Another time-of-flight positioning technique is two-way ranging (TWR). In TWR, a time-of-flight positioning unit and the mobile tag device perform ranging by exchanging ranging signals with to each other. The time-of-flight positioning unit, the mobile tag device, and/or the server then multiplies a time taken for the ranging signals to travel between the time-of-flight positioning unit and the mobile tag device by the speed of light to determine the distance between the time-of-flight positioning unit and the mobile tag device. TWR is also applicable to a plurality of mobile tag devices and/or a plurality of time-of-flight positioning units, as a plurality of mobile tag device-time-of-flight positioning pairs may perform the ranging.

In the time-of-flight positioning, either the one or more time-of-flight positioning units, or the one or more tag devices, may perform beaconing. In this case, the beaconing comprises broadcasting a signal comprising e.g. a device ID of the device performing the beaconing, for the purposes of the time-of-flight positioning. Beaconing in general is known in the art and further description is thus omitted.

In an embodiment, the time-of-flight positioning is ultra-wideband, UWB, time-of-flight positioning. UWB provides a range suitable for positioning in a gym environment. Its high bandwidth makes it very robust in a gym environment. UWB positioning also consumes very little energy. In an embodiment, the time-of-flight positioning is phase ranging.

Each wearable device of the one or more wearable devices 112 is associated with one of the one or more mobile tag devices. Each wearable device comprises a wireless communication unit, and a memory configured to store training data of the user. The wearable device 112 may be e.g. a wrist-worn portable training computer, or a heart rate monitor 114 as shown in FIG. 1.

In an embodiment, the wearable device comprises the mobile tag device that the wearable device is associated with. This ensures that the location of the wearable device is determined accurately, facilitates exchange of data between the mobile tag device and the wearable device, and may remove the need to store an association between the mobile tag device that the wearable device separately in a memory. Further, the user does not need to carry the mobile tag device as a separate device. Situations wherein the user is wearing their wearable device(s) but forgets to carry their mobile tag device are also eliminated.

In an embodiment, the wearable device 112, 114 comprises one or more wearable biosensors configured to measure the user to acquire training data, and the wearable device is configured to transmit the training data to the data collector device over the wireless connection. Alternatively or additionally, the wearable device 112 may be coupled to one or more external biosensors 114 configured to measure the user to acquire training data. The wearable device may be configured to transmit the training data to the data collector device over the wireless connection. The one or more wearable biosensors and/or the external biosensors may comprise one or more of the following: one or more heart activity sensors, one or more motion sensors, one or more location sensors, one or more swimming sensors, one or more power sensors, one or more bike sensors, and/or one or more temperature sensors, embodiments of which have been discussed in more detail above.

The system is configured to track locations of the one or more mobile tag devices with respect to the data collector devices in the gym as a result of the time-of-flight positioning. The locations of the one or more mobile tag devices may be inferred directly from the time-of-flight positioning, as the mobile tag devices take part in the time-of-flight positioning. The data collector devices may be configured to be disposed at fixed locations in the gym. The data collector devices may each be disposed at the location of the gym device or exercise spot the data collector device is associated with. The system may store the locations of the data collector devices and/or the exercise spots or gym devices in one or more or the following: the memory of the server computer, the memories of the wearable devices, and the memories of the data collector devices. The system may track the locations as distances or in a 2-dimensional or a 3-dimensional coordinate system, for example. The distances may be determined between the data collector devices or the time-of-flight positioning units and the mobile tag devices. In an embodiment, the data collector devices are configured to be disposed at the fixed locations of the time-of-flight positioning units; distances between the time-of-flight positioning units and the mobile tag devices therefore correspond to the distances between the data collector devices and the mobile tag devices.

In an embodiment, the system is configured to store a model comprising the locations of one or more of: the gym devices or exercise spots, the plurality of data collector devices, the pairing areas of the plurality of data collector devices, and the one or more time-of-flight positioning units. The system may be configured to use the model in tracking the locations of the one or more mobile tag devices with respect to the data collector devices. The model may be used to map the time-of-flight positioning data from the time-of-flight positioning performed by the time-of-flight positioning units and the mobile tag devices to locations of the mobile tag devices with respect to the data collector devices. In case the gym is re-arranged so that the locations gym devices or exercise spots, the plurality of data collector devices, the pairing areas of the plurality of data collector devices, and/or the one or more time-of-flight positioning units change, the system may be re-configured to account for the change(s). The reconfiguration may be performed by updating the model. The model may be stored in a memory of one or more of the following: the server computer, the wearable device(s), and the data collector devices.

The system may be initially calibrated using e.g. a mobile app of a smartphone. The mobile app may be used to scan device identifiers of the data collector devices and/or the time-of-flight positioning units to determine and store their locations. The locations may then be transmitted to the server for storing in the model described above, for example. The associations between the data collector devices and the gym devices or exercise spots may also be configured as a part of the calibration.

The system is configured to determine whether or not a location of a mobile tag device is within a pairing area of a data collector device. The pairing area may be a 2D area or a 3D volume, and/or it may be specified by coordinates in 2D or 3D space. The pairing areas of the data collector devices may be store in a memory of one or more of the following: the server computer, the data collector devices, and the wearable device.

Figure 5:
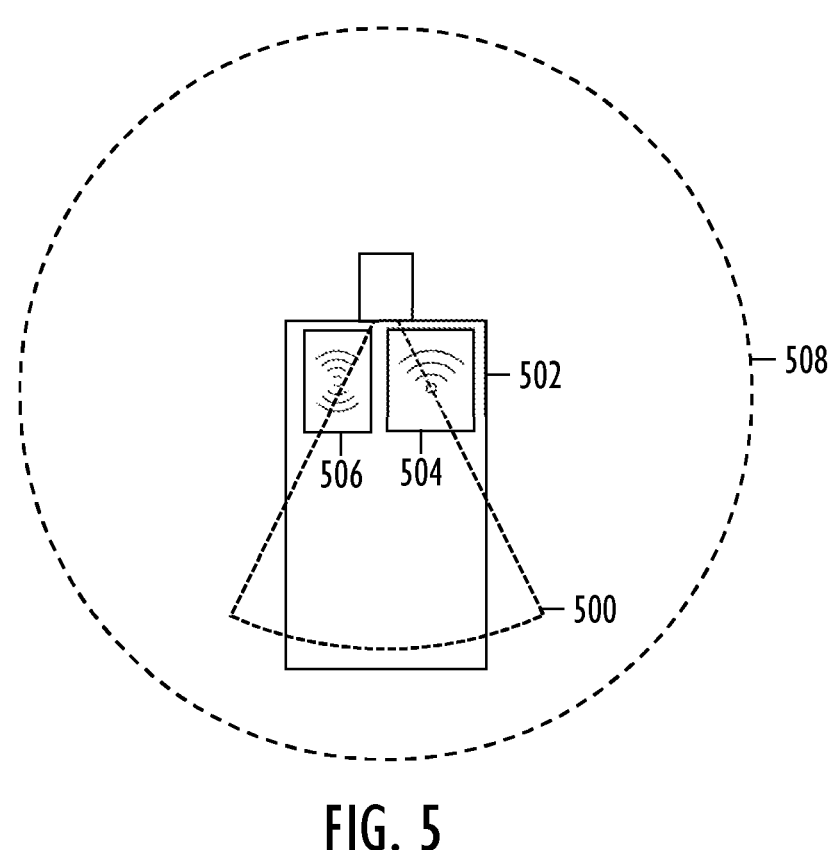
FIG. 5 illustrates embodiments of a pairing area.

In an embodiment, the pairing area is an exercise area of a gym device or an exercise spot, comprising an area in proximity of the gym device or exercise spot. Such exercise area is typically dedicated to a specific exercise and may involve the use of exercise equipment. The exercise area may be an area dedicated to an individual during the exercise. In this sense, the exercise area may be a personal exercise area. FIG. 5 depicts, from above, a pairing area 500 of a gym device 502 comprising a data collector device 504. The pairing area 500 may also be an example of an exercise area. The exercise area/pairing area 500 may be defined by the type of exercise to be carried out in the exercise area and/or by the type of the relevant gym device, such as a treadmill, stationary bicycle, or cross-training equipment. 508 may represent a range of the time-of-flight positioning unit 506, and/or a connectable range of the data collector device 504, i.e. a range within which the wearable device may form a wireless connection with the data collector device. The connectable range of the data collector device 504 may cover the pairing area 500 of the data collector device.

The dimensions of the personal exercise area may be such that the person is expected to stay within the bounds of the personal exercise area during the exercise. The range of the exercise area may be, for example, 1×1 meters or 1×2 meters. For example, in case of a treadmill, the exercise area may correspond to the area above the moving mat in which the user runs. In case of a stationary bicycle, the exercise area may comprise the area above the seat of the bicycle. In case of weightlifting at an exercise spot, the exercise area may comprise the area in which the specific weightlifting by the user 100 occurs. It should be noted though that in the case the user performs push-ups, squats, or alike, on a mat or on a floor, the exercise area may be the area in which the exerciser performs the push-ups or alike. In this case, there may not be any specific gym device with which the exercise is performed, but instead an exercise spot where the user performs the exercises. A data collector device 504 may be located near or in that exercise spot or exercise area in order to acquire training data while the user is exercising at the exercise spot/area. Additionally, a time-of-flight positioning unit 506 may be located near or in that exercise spot or exercise area in order for the time-of-flight positioning unit to detect the presence of a mobile tag device of the exerciser. The data collector device and/or the time-of-flight positioning unit may be mounted on a near-by wall or a ceiling, for example. The gym device may also provide a mounting element of the data collector device and/or the time-of-flight positioning unit, for example.

Further, in addition to proximity limitations, the pairing area and/or the exercise area may also have angular limitations so that the exercise area is present only in one predetermined direction from the gym device. The predetermined direction may be specified with an angular spread of certain number of degrees. For example, in case of the bicycle, the proximity area in front of the bicycle may not be part of the exercise area. In FIG. 5, gym device 502 may be a treadmill, and the pairing area 500 covers a part of the treadmill and some areas along the long sides of the treadmill. Given that the data collector device 504 may be integrated to a console of the treadmill and is shown at a first end of the treadmill, the user is likely to enter the treadmill from the areas outside the treadmill that are covered by the pairing area 500. Pairing of the user's wearable device with the data collector device 504 may thus begin already as the user steps on the treadmill, and the pairing is likely to be completed by the time the user begins their workout on the treadmill, and training data may be exchanged from the beginning of the workout.

In other words, the exercise area and/or pairing area is the area in which the user is expected to be while performing the exercise with the corresponding gym device or exercise spot. The exercise area may be empirically derived for each type of gym device or exercise spot.

If the location of the mobile tag device is within the pairing area, the system triggers establishment of a wireless connection between a wireless communication unit of the data collector device and a wireless communication unit of a wearable device associated with the mobile tag device. In an embodiment, the wireless connection utilizes one of the following short-range device-to-device communication technologies: Bluetooth, Bluetooth Low Energy, wireless local area network (WLAN), ANT, ANT+, or IEEE 802.15.4.

The system is further configured transmit training data between at least two of the data collector device, the wearable device, and the server computer. In an embodiment, the system is configured to transmit training data between the data collector device and the wearable device over the (established) wireless connection. The data collector device may transmit training data to the wearable device, and/or the wearable device may transmit training data to the data collector device. In an embodiment, establishment of the wireless connection triggers training data transfer between the data collector device and/or the wearable device, and the server computer. The gym device associated with the data collector device may be configured to receive a training (session) plan as the training data from the server, and to adjust settings of the gym device according to the training (session) plan. The user ID and/or a device ID associated with the user ID transferred as a part of the training data may be used to identify a correct training plan from the server. For example, when the gym device associated with the data collector device is a treadmill, establishment of the wireless connection may trigger transfer of a running program or a running session plan as a part of the training data from the server to the treadmill. The treadmill may be configured to utilize the running program or a running session plan to control settings of the treadmill while the user is exercising on the treadmill, to assist the user in following the running program or a running session plan.

A separate wireless connection may be used for communication between the server computer, and the wearable device(s) and/or the data collector devices.

Each of the data collector devices, the wearable devices, and the mobile tag devices may have an associated device ID. The device ID may be used to identify the relevant device for wireless communication purposes or for associations with user ID(s) of the one or more users. In an embodiment, the mobile tag device is configured to store a device ID of the wearable device associated with the mobile tag device, and to transmit the device ID of the wearable device to the one or more time-of-flight positioning units. Transmitting the device ID may be performed as a part of and/or during the time-of-flight positioning. The time-of-flight positioning unit(s) may transmit the device ID of the wearable device to a data collector device whose pairing area the mobile tag device is located in. This may facilitate establishment of the wireless connection between the wearable device to a data collector device, as the data collector may use the device ID of the wearable device in establishing the wireless connection. Transmitting the device ID to the data collector device may be done using wired and/or wireless connections as described herein. In an embodiment, the time-of-flight positioning unit is configured to store a device ID of a data collector device disposed in the fixed location of the time-of-flight positioning unit, and to transmit the device ID of the data collector device to the one or mobile tag devices during the time-of-flight positioning. Transmitting the device ID may be performed as a part of and/or during the time-of-flight positioning. The mobile tag device(s) may transmit the device ID of the data collector device to the wearable device associated with the mobile tag device. This may facilitate establishment of the wireless connection between the wearable device to a data collector device, as the wearable may use the device ID of the data collector device in establishing the wireless connection. Transmitting the device ID to the data wearable device may be done using wired and/or wireless connections as described herein. The device ID(s) of the wearable device and data collector device may similarly be transmitted from the mobile tag device and/or the time-of-flight positioning units to the server for the purpose of triggering the establishment of the wireless connection, so that the server may send a command to establish the wireless connection to the correct data collector device and/or wearable device.

Figure 6:
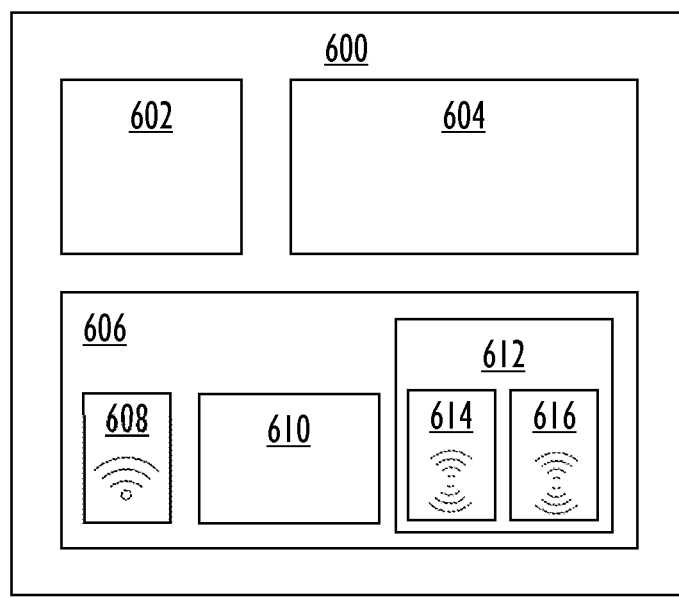
FIG. 6 illustrates embodiments related to a data collector device and a time-of-flight positioning unit.

FIG. 6 illustrates embodiments of a data collector device 606. A console 600 of a gym device may comprise a controller 602 and a user interface 604. The data collector device 606 comprises a wireless communication unit 608, and a microcontroller unit (MCU) 610. In an embodiment, the data collector device comprises a time-of-flight positioning unit 612. This may simplify communication between the data collector device and the time-of-flight positioning unit, and facilitate positioning of the data collector device with respect to the mobile tag devices, or tracking the locations of the mobile tag devices with respect to the data collector device.

In an embodiment, at least one time-of-flight positioning unit 612 of the one or more time-of-flight positioning units comprises at least two time-of-flight positioning sensors 614, 616 configured to conduct the time-of-flight positioning. In an embodiment, the time-of-flight positioning sensors are time-of-flight positioning antennas. As discussed above, two time-of-flight positioning units may track the location of the mobile tag device to a pair of points, or in some cases, a single point in 2D space. A technical effect is that the time-of-flight positioning unit may alone locate the mobile tag device with sufficient accuracy. The time-of-flight positioning unit may be located at the fixed location of a gym device, for example. The time-of-flight positioning unit may determine when the user carrying the mobile tag device is in close enough proximity to the gym device to establish a wireless connection between a data collector device associated with the gym device, and the wearable device.

Figure 7:
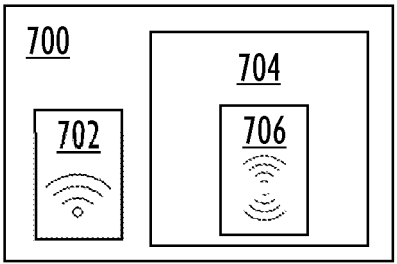
FIG. 7 illustrates embodiments related to a wearable device and a mobile tag device.

FIG. 7 illustrates embodiments of a wearable device 700 comprising a wireless communication unit 702. In an embodiment, the wearable device comprises the mobile tag device 704. The mobile tag device comprises a time-of-flight positioning unit 706.

In an embodiment, the system is configured to: detect if the determined location of the mobile tag device is no longer in the pairing area of the data collector device, and if the determined location is no longer in the pairing area, terminate the wireless connection. This may free up the wearable device and the data collector device to form another wireless connection with another device.

Figure 8:
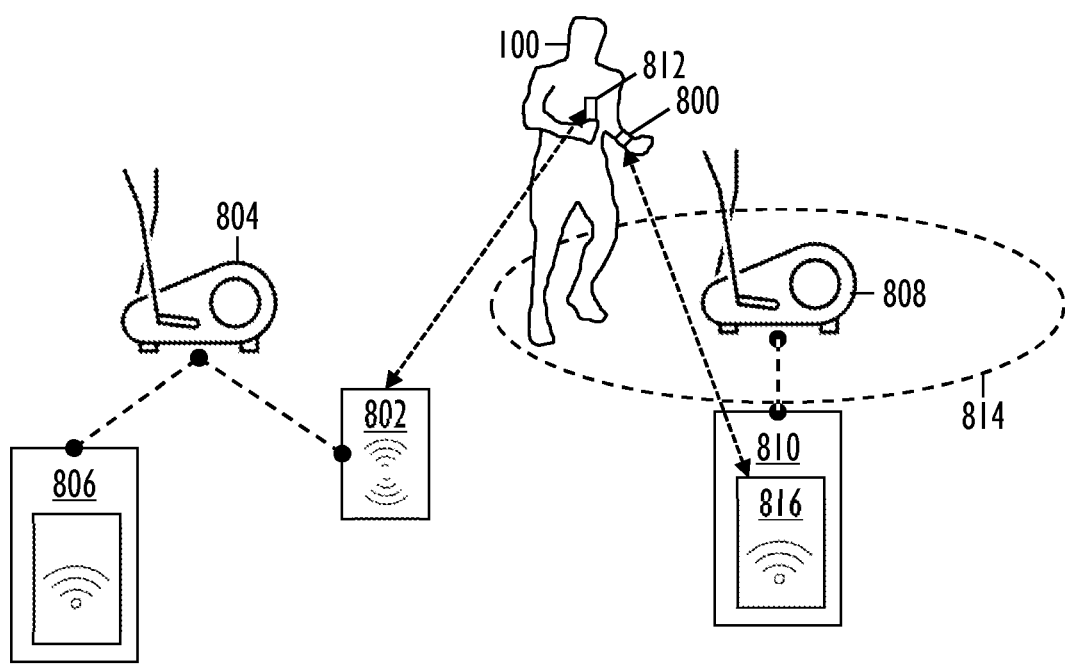
FIG. 8 illustrates embodiments related to a location of a time-of-flight positioning unit.

FIG. 8 illustrates embodiments related to a specific location of a time-of-flight positioning unit at the location of a gym device. In an embodiment, the one or more time-of-flight positioning units comprises a time-of-flight positioning unit 802 configured to conduct the time-of-flight positioning and to be disposed at a fixed location of a first gym device 804 or exercise spot associated with a first data collector device 806, and a fixed location of a second gym device 808 or exercise spot associated with a second data collector device 810 has no time-of-flight positioning unit, and wherein the system of configured to: determine, on the basis of the time-of-flight positioning performed by the time-of-flight positioning unit 802, whether or not the location of the mobile tag device 812 is within a pairing area 814 of the second data collector device; and if the location is determined to be within the pairing area, trigger establishment of a wireless connection between a wireless communication unit 816 of the second data collector device and the wireless communication unit of the wearable device 800 associated with the mobile tag device. Each gym device therefore does not need to have its own dedicated time-of-flight positioning unit, but the time-of-flight positioning unit at another gym device may be used to locate the mobile tag device to another gym device.

In an embodiment, the one or more mobile tag devices and/or the one or more time-of-flight positioning units are configured to transmit time-of-flight positioning data, and the server computer is configured to receive the time-of-flight positioning data, and to track the locations of the one or more mobile tag devices with respect to the data collector devices and determine whether or not a location of a mobile tag device is within a pairing area of a data collector device on the basis of the time-of-flight positioning data, and to trigger establishment of the wireless connection by sending a command to establish the wireless connection to the data collector device and/or the wearable device if the location is determined to be within the pairing area. Transmitting the time-of-flight positioning data may be implemented with wired or wireless connections from the time-of-flight positioning units to the server computer, and with a wireless connection from the one or more mobile tag devices to the server. In the above embodiment, the heavy processing of the time-of-flight positioning data to track the locations of the one or more mobile tag devices is performed by the server computer. This centralized approach allows may require less processing power of the data collector devices and/or the wearable devices.

In an embodiment, at least one of the plurality of data collector devices is configured to receive the time-of-flight positioning data, and to re-transmit the time-of-flight positioning data to the server computer. In an embodiment, the plurality of data collector devices are configured to receive the time-of-flight positioning data, and to re-transmit the time-of-flight positioning data to the server computer. Referring to FIG. 3, the data collector device 310 may receive time-of-flight positioning data from time-of-flight positioning unit 314 e.g. via an interface of the gym device 302. In an embodiment, the one or more time-of-flight positioning units are configured to receive the time-of-flight positioning data from the one or more mobile tag devices, and to and to re-transmit the time-of-flight positioning data received from the one or more mobile tag devices to the server computer. For example. time-of-flight positioning unit 322 of FIG. 3 may receive time-of-flight positioning data from tag 336, and re-transmit it to the server 350 using wireless communication unit 332.

Technical effects of the above embodiments include reduced transmission power requirements for the one or more mobile tag devices and/or the one or more time-of-flight positioning units. The data collector devices and/or the one or more time-of-flight positioning units may act as gateways as they relay the time-of-flight positioning data to the server computer. Additional transmission power may be provided to the data collector devices and/or the one or more time-of-flight positioning units if needed for the re-transmission.

In an embodiment, a wearable device of the one or more wearable devices is configured to receive time-of-flight positioning data from a mobile tag device associated with the wearable device, and to track a location of the wearable device with respect to the data collector devices on the basis of the time-of-flight positioning data, and to determine, on the basis of the tracking, whether or not the location is within a pairing area of a data collector device, and to trigger establishment of a wireless connection between the wearable device and the data collector device if the location is determined to be within the pairing area. The wearable device may trigger establishment of the wireless connection by initializing the wireless connection, for example. The wearable device may receive the time-of-flight positioning data from the mobile tag device via a wired or wireless connection, for example. In the embodiment of FIG. 7, the mobile tag device 704 is comprised in the wearable device 700, and the wearable device may receive the time-of-flight positioning data from the mobile tag device 704 via direct electrical connections, for example.

The above embodiment has the advantage of reduced infrastructure needs related to the time-of-flight positioning units. As the wearable device receives time-of-flight positioning data from the mobile tag device and performs the location tracking and subsequent steps, the time-of-flight positioning units do not necessarily need to participate in any of the method steps other than the time-of-flight positioning together with the mobile tag device(s).

In an embodiment, a data collector device of the plurality of data collector devices is configured to receive time-of-flight positioning data from the one or more time-of-flight positioning units, and to track the locations of the one or more mobile tag devices with respect to the data collector device, and to determine, on the basis of the tracking, whether or not a location of a mobile tag device is within a pairing area of the data collector device on the basis of the time-of-flight positioning data, and if the location is determined to be within the pairing area, trigger establishment of a wireless connection between the data collector device and a wearable device associated with the mobile tag device. The data collector device may receive the time-of-flight positioning data from the one or more time-of-flight positioning units via a wired or wireless connection, for example. In the embodiment of FIG. 6, the data collector device 606 comprises the time-of-flight positioning unit 612, and the data collector device may receive the time-of-flight positioning data from the time-of-flight positioning unit via direct electrical connections, for example.

In an embodiment, the data collector device is configured to track the locations of the one or more mobile tag devices in the pairing area of the data collector device. Each data collector device may track the locations of the one or more mobile tag devices only in the pairing area of the data collector device. The entire gym therefore need not be monitored, which may save software and hardware resources.

In relation to the above embodiments, when the wearable device comprises the mobile tag device, the mobile tag device may transmit the time-of-flight positioning data using the wireless communication unit of the wearable device. When the data collector device comprises the time-of-flight positioning unit, or the gym device comprises the data collector device and the time-of-flight positioning unit, the time-of-flight positioning unit may transmit the time-of-flight positioning data using the wireless communication unit of the data collector device. As shown in FIG. 3, the time-of-flight positioning unit(s) 318, 320, 322, 324 may comprise or be coupled to wireless communication unit(s) 328, 330, 332, 334, and the time-of-flight positioning unit(s) may transmit the time-of-flight positioning data using the wireless communication unit(s).

Figure 9:
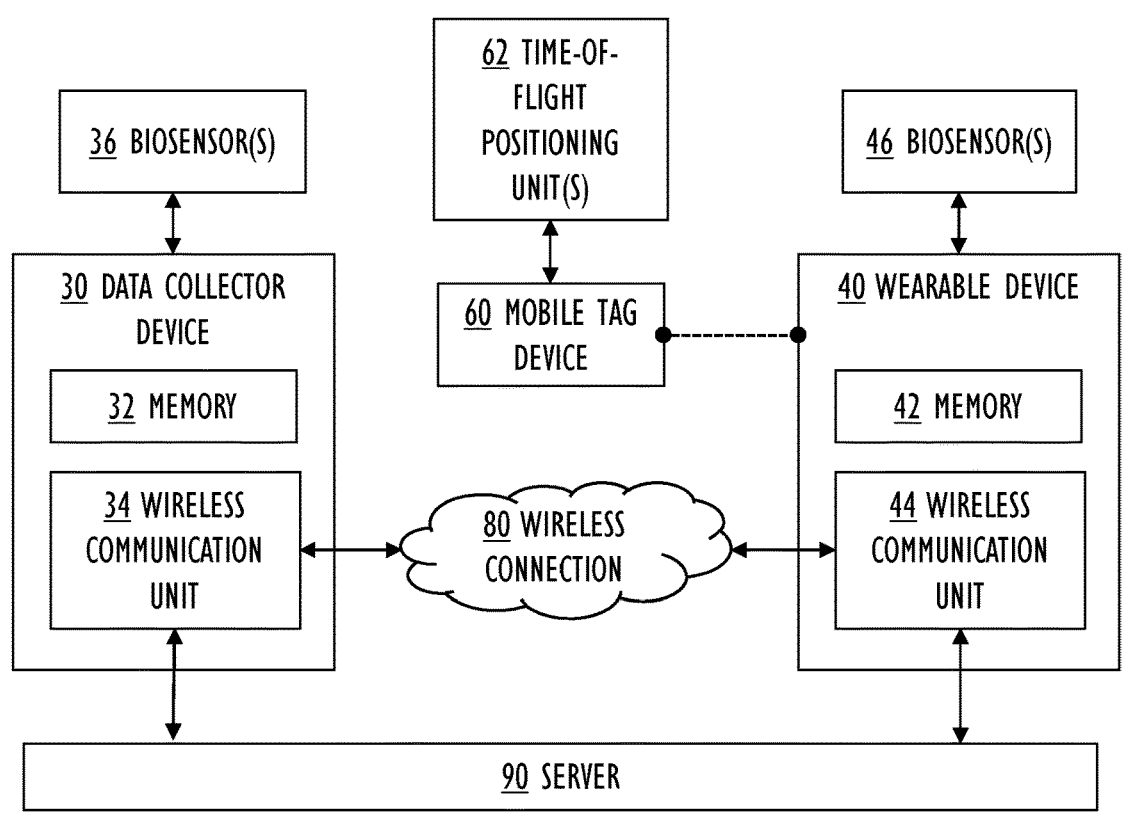
FIG. 9 is a block diagram illustrating embodiments of a system.
Figure 10:
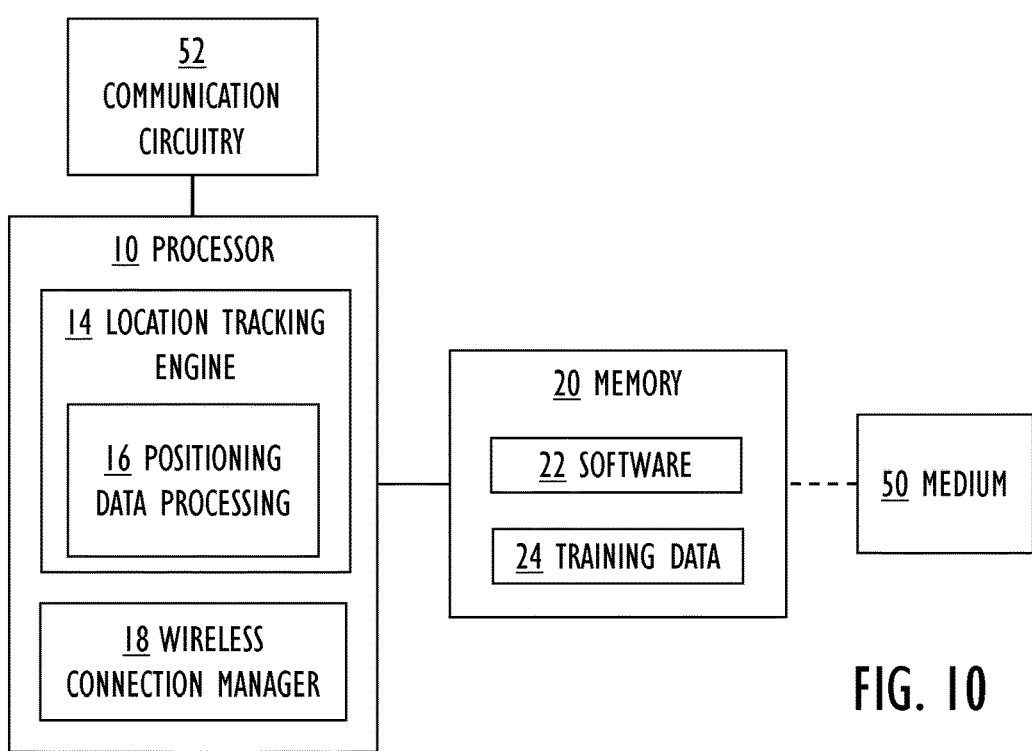
FIG. 10 is a block diagram illustrating embodiments of a device.

FIG. 9 illustrates a block diagram of a system according to an embodiment of the invention, and FIG. 10 illustrates a block diagram of a device comprising a processing system configured to perform the method of FIG. 2 or any one of the embodiments thereof described above. The device may be the data collector device 30, the wearable device 40, or the server computer 90, all shown in FIG. 9. The processing system may comprise at least one processor 10 and at least one memory 20.

The processor 10 may comprise a location tracking engine 14 configured to track the locations of the one or more mobile tag devices by controlling the procedure of FIG. 2 or any one of the embodiments thereof. The location tracking engine 14 may comprise a positioning data processing circuitry 16 configured to acquire time-of-flight positioning data for the purposes of tracking the locations of the one or more mobile tag devices with respect to the data collector devices. In embodiments where the device is the wearable device 40, the circuitry 16 may collect the time-of-flight positioning data from the mobile tag device 60 associated with the wearable device 40. As described above, the mobile tag device may be provided in the wearable device. In embodiments where the device is the data collector device 30, the circuitry 16 may collect the time-of-flight positioning data from the time-of-flight positioning unit(s) 62. As described above, a gym device may comprise both the data collector device 30 and the time-of-flight positioning unit 62. The processor 10 may further comprise a wireless connection manager 18 configured to trigger establishment of the wireless connection 80 between the data collector device 30 and the wearable device 40 according to the principles described above and on the basis of the location tracking performed by the location tracking engine 14.

The device may comprise a communication circuitry 52 connected to the processor 10. When the device is the data collector device 30, the communication circuitry 52 may be the wireless communication unit 34 of the data collector device 30. When the device is the wearable device 40, the communication circuitry 52 may be the wireless communication unit 44 of the wearable device 40. The communication circuitry 52 may comprise hardware and software suitable for supporting Bluetooth® communication protocol such as Bluetooth Smart specifications. It should be appreciated that other communication protocols are equivalent solutions as long as they are suitable for establishing the wireless connection 80 between the wireless communication unit 34 of the data collector device 30 and the wireless communication unit 44 of the wearable device 40, or suitable for measurement scenarios described in this document. Further, when the device is the data collector device 30, the communication circuitry 52 may be used to establish a wireless connection between the data collector device 30 and the biosensors 36, and when the device is the wearable device, the communication circuitry 52 may be used to establish a wireless connection between the wearable device 40 and the biosensors 46. The communication circuitry may comprise a radio modem and appropriate radio circuitries for establishing a communication connection between the server computer 90, the wearable device 40, and/or the data collector device 30, depending on the implementation of the device. Suitable radio protocols may include IEEE 802.11-based protocols or cellular communication protocols. In case the device is the server computer, the communication circuitry 52 may comprise one or more computer network circuits operating, for example, according to Ethernet protocol. The processor 10 may use the communication circuitry 52 to transmit and receive frames or data according to the supported wireless communication protocol. The frames may carry a payload data comprising the above-described time-of-flight positioning data measured by the time-of-flight positioning unit(s) 62 and the mobile tag device(s) 60, training data from the biosensors 36 to the data collector device 30 and/or from the biosensors 46 to the wearable device 40, and/or training data between the devices 30, 40, and 90.

The memory 20 may store a computer program product 22 defining computer program instructions for carrying out the method of FIG. 2 or any one of the embodiments thereof. The memory may further store training data 24 of the user 100 storing personal characteristics of the user 100, e.g. age, weight, the fitness level, etc. The memory may further store a measurement database comprising the measurement data computed during and/or after the exercises performed by the user, and/or other embodiments of the training data as described herein. The memory 20 may be the memory 32 of the data collector device 30, the memory 42 of the wearable device 40, or the memory of the server computer 90.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIG. 2 may be carried out by a system comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor, the memory, and the computer program code form processing means or comprises one or more computer program code portions for carrying out one or more operations according to any one of the embodiments of FIG. 2 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, other electronic units designed to perform the functions described herein, or a combination thereof. For firmware or software, the implementation can be carried out through modules of at least one chipset (e.g, procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIG. 2 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium 50 readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Even though the invention has been described with reference to one or more embodiments according to the accompanying drawings, it is clear that the invention is not restricted thereto but may be modified in several ways within the scope of the appended claims. All words and expressions should be interpreted broadly, and they are intended to illustrate, not to restrict, the embodiments. It will be obvious to a person skilled in the art that, as technology advances, the inventive concept may be implemented in various ways.

What is claimed is:

1. A system comprising:
a server computer comprising at least one processor and at least one memory configured to store training data of one or more users;
a plurality of data collector devices, each of the plurality of data collector devices being associated with a gym device or an exercise spot of a gym,
wherein
each data collector device comprises a wireless communication unit, and a memory configured to store training data of a user;
one or more time-of-flight positioning units configured to be disposed at fixed locations in the gym and conduct time-of-flight positioning;
one or more mobile tag devices, each mobile tag device comprising a time-of-flight positioning unit configured to conduct the time-of-flight positioning together with the time-of-flight positioning units at the fixed locations; and
one or more wearable devices, wherein each wearable device is associated with one of the one or more mobile tag devices, and each wearable device comprises a wireless communication unit, and a memory configured to store training data of the user,
wherein the system is configured to perform operations comprising:
tracking locations of the one or more mobile tag devices with respect to the data collector devices in the gym as a result of the time-of-flight positioning;
determining, on the basis of the tracking, whether or not a location of a mobile tag device is within a pairing area of a data collector device; and
when the location is determined to be within the pairing area, triggering establishment of a wireless connection between a wireless communication unit of the data collector device and a wireless communication unit of a wearable device associated with the mobile tag device, and transmitting training data between at least two of the data collector device, the wearable device, and the server computer.

2. The system of claim 1, wherein the time-of-flight positioning is ultra-wideband (UWB) time-of-flight positioning.

3. The system of claim 1, wherein the wearable device comprises the mobile tag device that the wearable device is associated with.

4. The system of claim 1, wherein the wearable device comprises one or more wearable biosensors configured to measure the user to acquire training data, and the wearable device is configured to transmit the training data to the data collector device over the wireless connection.

5. The system of claim 1, wherein the data collector device is coupled to one or more biosensors of a gym device associated with the data collector device, the one or more biosensors configured to measure the user to acquire training data, and wherein the data collector device is configured to transmit the training data to the wearable device over the wireless connection and/or to the server computer.

6. The system of claim 1, wherein each gym device or exercise spot associated with a data collector device is disposed in the gym such that the gym device or exercise spot is at a unique distance from a time-of-flight positioning unit with respect to the other gym devices and exercise spots, and the pairing area of the data collector device associated with the gym device or exercise spot comprises a range of distances between the mobile tag device and the time-of-flight positioning unit including the unique distance.

7. The system of claim 1, wherein pairing areas of the plurality of data collector devices are non-overlapping.

8. The system of claim 1, wherein at least one time-of-flight positioning unit of the one or more time-of-flight positioning units comprises at least two time-of-flight positioning sensors configured to conduct the time-of-flight positioning.

9. The system of claim 1, wherein the one or more time-of-flight positioning units comprises a plurality of time-of-flight positioning units that are configured to be disposed at fixed locations of each gym device or exercise spot associated with the plurality of data collector devices.

10. The system of claim 1, wherein the one or more time-of-flight positioning units are configured to be disposed at fixed locations separate from the locations of each gym device or exercise spot associated with the plurality of data collector devices.

11. The system of claim 1, wherein the one or more time-of-flight positioning units comprises a time-of-flight positioning unit configured to conduct the time-of-flight positioning and to be disposed at a fixed location of a first gym device or exercise spot associated with a first data collector device, and a fixed location of a second gym device or exercise spot associated with a second data collector device has no time-of-flight positioning unit, and wherein the system is configured to perform operations comprising:
determining, on the basis of the time-of-flight positioning performed by the time-of-flight positioning unit, whether or not the location of the mobile tag device is within a pairing area of the second data collector device; and
if the location is determined to be within the pairing area, triggering establishment of a wireless connection between a wireless communication unit of the second data collector device and the wireless communication unit of the wearable device associated with the mobile tag device.

12. The system of claim 1, wherein the one or more mobile tag devices and/or the one or more time-of-flight positioning units are configured to transmit time-of-flight positioning data, and the server computer is configured to receive the time-of-flight positioning data, and to track the locations of the one or more mobile tag devices with respect to the data collector devices and determine whether or not a location of a mobile tag device is within a pairing area of a data collector device on the basis of the time-of-flight positioning data, and to trigger establishment of the wireless connection by sending a command to establish the wireless connection to the data collector device and/or the wearable device if the location is determined to be within the pairing area.

13. The system of claim 12, wherein at least one of the plurality of data collector devices is configured to receive the time-of-flight positioning data, and to re-transmit the time-of-flight positioning data to the server computer.

14. The system of claim 1, wherein a wearable device of the one or more wearable devices is configured to receive time-of-flight positioning data from a mobile tag device associated with the wearable device, and to track a location of the wearable device with respect to the data collector devices on the basis of the time-of-flight positioning data, and to determine whether or not the location is within a pairing area of a data collector device, and to trigger establishment of a wireless connection between the wearable device and the data collector device if the location is determined to be within the pairing area.

15. The system of claim 1, wherein a data collector device of the plurality of data collector devices is configured to receive time-of-flight positioning data from the one or more time-of-flight positioning units, and to track the locations of the one or more mobile tag devices with respect to the data collector device, and to determine whether or not a location of a mobile tag device is within a pairing area of the data collector device on the basis of the time-of-flight positioning data, and if the location is determined to be within the pairing area, trigger establishment of a wireless connection between the data collector device and a wearable device associated with the mobile tag device.

16. A method comprising:

conducting time-of-flight positioning;

by one or more mobile tag devices together with one or more time-of-flight positioning units, wherein the one or more time-of-flight positioning units are configured to be disposed at fixed locations in a gym;

tracking locations of the one or more mobile tag devices with respect to a plurality of data collector devices in the gym as a result of the time-of-flight positioning, wherein each of the plurality of data collector devices is associated with a gym device or an exercise spot of a gym and configured to store training data of a user;

determining, on the basis of the tracking, whether or not a location of a mobile tag device is within a pairing area of a data collector device; and when the location is determined to be within the pairing area, triggering establishment of a wireless connection between a wireless communication unit of the data collector device and a wireless communication unit of a wearable device configured to store training data of the user and associated with the mobile tag device, and transmitting training data between at least two of the data collector device, the wearable device, and a server computer configured to store training data of one or more users.

* * * * *